United States Patent
Lehmann

(10) Patent No.: US 7,654,981 B2
(45) Date of Patent: Feb. 2, 2010

(54) REMOVING DEVICE FOR INJECTION NEEDLES

(75) Inventor: Hans-Ulrich Lehmann, Bellmund (CH)

(73) Assignee: TecPharma Licensing AG, Burgdorf (CH)

( * ) Notice: Subject to any disclaimer, the term of this patent is extended or adjusted under 35 U.S.C. 154(b) by 276 days.

(21) Appl. No.: 11/137,133

(22) Filed: May 25, 2005

(65) Prior Publication Data
US 2005/0273053 A1  Dec. 8, 2005

Related U.S. Application Data

(63) Continuation of application No. PCT/CH03/00760, filed on Nov. 17, 2003.

(30) Foreign Application Priority Data
Nov. 26, 2002 (DE) ............................. 102 55 134

(51) Int. Cl.
*A61M 5/00* (2006.01)
(52) U.S. Cl. .................................... 604/110; 206/366
(58) Field of Classification Search ................ 604/110, 604/181, 192, 263; 206/364–366
See application file for complete search history.

(56) References Cited

U.S. PATENT DOCUMENTS

| 4,875,265 | A | * | 10/1989 | Yoshida | ....................... 29/240 |
|---|---|---|---|---|---|
| 5,312,346 | A | * | 5/1994 | Han | ........................... 604/110 |
| 5,347,078 | A | * | 9/1994 | Eckels | ...................... 588/249.5 |
| 5,519,931 | A | * | 5/1996 | Reich | ......................... 29/426.3 |
| 6,036,671 | A |   | 3/2000 | Frey | |
| 6,062,001 | A |   | 5/2000 | Kunik | |

FOREIGN PATENT DOCUMENTS

| DE | 27 40 335 | 3/1979 |
|---|---|---|
| DE | 197 40 187 C1 | 4/1999 |
| DE | 100 46 279 A1 | 4/2002 |
| EP | 0 787 501 A2 | 8/1997 |
| FR | 2 760 647 | 9/1998 |
| WO | WO 97/40869 | 11/1997 |
| WO | WO 01/87387 A1 | 11/2001 |

* cited by examiner

*Primary Examiner*—Kevin C Sirmons
*Assistant Examiner*—Bhisma Mehta
(74) *Attorney, Agent, or Firm*—Dorsey & Whitney LLP; David E. Bruhn

(57) ABSTRACT

A device for removing a needle unit from an injection device, the device for removing including an opening for receiving the needle unit and a locking structure generally associated with the opening, the locking structure formed in at least one rim area along the circumference of the opening, such that the needle unit can be moved in an insertion direction through the opening after it has been inserted into the opening, and when the needle unit is moved counter to the insertion direction, it establishes a locking connection with the locking structure. In one embodiment, the invention includes a container for receiving and containing at least one used needle unit.

16 Claims, 7 Drawing Sheets

REMOVING DEVICE FOR INJECTION NEEDLES

CROSS-REFERENCE TO RELATED APPLICATIONS

This application is a continuation of International Application No. PCT/CH2003/000760, filed on Nov. 17, 2003, which claims priority to German Application No. 102 55 134.0, filed on Nov. 26, 2002, the contents of which are incorporated herein by reference in their entirety.

BACKGROUND

The invention relates to a removing device for removing, detaching or unconnecting injection needles or needle units from an injection or infusion device, in particular an injection pen, and to removing device integrated with a container for receiving, storing and disposing of used needle units and/or needles.

Injection pens are used for subcutaneously administering an active agent, wherein using the pen and dosing the active agent should be sufficiently simple and reliable that administering may be performed not only by medically trained individuals but also by laymen and/or patients. Using typical known pens, the required dosage amount can be set, an injection needle injected into the selected injection area and the active agent dispensed by simple hand movements.

Generally speaking, however, each injection needle or cannula should only be used for an injection once, whereas the injection pen can be repeatedly used and reloaded. In most cases, therefore, an injection needle is arranged in a needle unit which can be removed from the injection pen once the needle has been used, such that a new needle unit can be inserted into the pen for the next administering.

Removing the needle unit, however, harbours a certain danger of injury. After the active agent has been administered, the injection needle is exposed and, typically, a protective cover must be put in place or attached.

An injection needle container for storing needle units is known from U.S. Pat. Nos. 5,873,462 and 5,829,589. The disclosed containers comprise an individual hollow space, open to one side, for each needle unit, from which a needle unit can be removed and into which it can be placed again. For returning the needle unit, once used, into the hollow space of the container, U.S. Pat. No. 5,873,462 describes a blocking device comprising a sealing flange on the opening of the hollow space and a sealing ring on the needle unit. When the needle unit is inserted into the hollow space with the aid of the injection pen, the flange and the ring establish a fixed connection, such that the needle unit can be removed from the pen. A collar running inwardly is formed at a suitable level in the hollow space, the needle unit resting on said collar when it is inserted. The needle unit is held fixed in its position in the hollow space by the blocking device and the collar. In U.S. Pat. No. 5,829,589, the blocking device for the needle unit in the hollow space is formed as a screw connection.

SUMMARY

It is an object of the present invention to provide a removing device which facilitates removing a needle unit from an injection pen, reduces the resultant danger of injury and infection, and prevents contact with the needle unit.

It is also the object of the invention to provide a container for storing used needle units, into which a needle unit can be safely and easily inserted, without the risk of injury or infection when removing the used needle unit from the injection pen and placing it into the container.

Objects of the present invention are addressed by providing a device for removing a needle unit from an injection device, the device for removing including an opening for receiving the needle unit and a locking structure generally associated with the opening, the locking structure formed in at least one rim area along the circumference of the opening, such that the needle unit can be moved in an insertion direction through the opening after it has been inserted into the opening, and when the needle unit is moved counter to the insertion direction, it establishes a locking connection with the locking structure. In one embodiment, the invention includes a container for receiving and containing at least one used needle unit, wherein the device for removing is operably associated with the container to provide a system for removing and storing or disposing of needles and/or needle units. The container may be generally can-like, having an opening for being operably associated with the removing device. The container may be any suitable shape, it may be disposable or reuseable, and it may be made of any suitable material.

In accordance with the present invention, a device for removing a needle unit from an injection device such as an injection pen comprises an opening for receiving the needle unit, and a blocking means. In at least one rim area along the circumference of the opening, the blocking means is formed such that the needle unit can be moved in the insertion direction once it has been inserted into the opening. When the needle unit moves counter to the insertion direction, however, it establishes a fixed blocking connection with the blocking means in the opening, such that the needle unit is blocked by said blocking connection.

The removing device in accordance with the invention ensures that a needle unit is simply and quickly removed from an injection pen, in that the needle unit can be removed from the injection pen by a simple hand operation, for which it is merely necessary to insert the end of the injection pen with the needle unit into the opening of the removing device. By gently pressing in manually, the blocking connection between the needle unit and the blocking device in the rim of the opening is established. The injection pen is extracted against only a small resistance which arises from detaching the needle unit from the pen. This resistance force is less than the force with which the needle unit is held in the blocking device, such that when the injection pen is extracted, the needle unit can be detached from the pen. In this way, the needle unit can be removed from the injection pen without a user coming into contact with the needle unit, since it lies inside the opening during the whole removing process.

In a preferred example embodiment, the blocking device extends over the whole circumference of the rim of the opening, which is advantageously adjusted to the outer circumference of a needle unit. The blocking device can therefore engage with the entire outer circumference of the needle unit. In order to form the blocking device, a first edge of the rim of the opening in the insertion direction preferably exhibits a larger circumference than a second edge of the opening. The blocking device can for example be formed by a rim of the opening which is conically constricted in the insertion direction. The circumference of the second edge of the opening is adjusted to the outer circumference of the needle unit, such that a clamping connection arises between the opening and the needle unit. Due to the conically constricted gradient of the rim of the opening, the needle unit is easily centred in the opening and can be clamped into the blocking connection against only a small resistance.

The second edge then acts on the needle unit as a sort of holding claw. The holding force of the blocking device is then dimensioned to be just large enough that the resistance against removing the needle unit from the injection pen is overcome. Generally speaking, a force of a few newtons is sufficient.

It is also possible to provide the blocking device using one or more rubber elements arranged on the rim surface of the opening. When the needle unit is pressed into the blocking device, the rubber is compressed and establishes a clamping connection with the needle unit.

Alternatively, the blocking device can also be realised on the opening by a locking means which co-operates with a complementary locking means on the needle unit. This can utilise the advantages of the invention in a system consisting of a removing device and an injection pen including a needle unit. The locking means of the blocking device can for example be realised by a number of grooves arranged in the circumferential direction on the rim surface of the opening. The complementary locking means of the needle unit can accordingly be provided by a number of protrusions arranged in the circumferential direction on the outer surface of the needle unit, wherein care merely needs to be taken that the blocking connection between the blocking device and the needle unit can at least be broken by a needle unit subsequently inserted into the opening and that the holding force of the blocking connection is greater than the force necessary to release the needle unit from the injection pen. It is also possible to use viewing windows, already provided in the needle unit, as locking means and to adjust the locking means of the blocking device, e.g. knobs in the circumferential surface of the rim of the opening, to the arrangement of the viewing window on the needle unit.

Lastly, the blocking device can be provided by a rotational connection between the opening and the needle unit. To this end, at least one but preferably two, at least partially obliquely running guiding grooves are preferably provided in the rim of the opening. A pin arranged laterally on the needle unit is guided through the blocking device along the guiding groove, wherein a number of pins is provided corresponding to the number of grooves on the needle unit.

The guiding groove begins on the first edge of the rim surface of the opening in the insertion direction and leads into a second edge, such that an entry and exit groove part arises for the pins of the needle unit. Between these groove parts, a middle part of the groove having a blocking effect is provided and for this purpose exhibits a greater inclination, for example with respect to the axis of the guiding element, than the entry and exit groove part. It would also be conceivable to form this groove part transverse to the axial direction, i.e. in the circumferential direction. The entry part and the exit part of the groove are therefore arranged offset with respect to each other and connected by the middle blocking part of the groove which runs obliquely or transversely.

When the injection pen is inserted, the pins of the needle unit engage with the guiding grooves. A slight pressure guides the pins along the grooves and rotates them with respect to the entry position, wherein a sort of locking connection arises within the oblique middle part of the groove, for example by a reverse rotational block in the form of a protrusion in the groove. As the injection pen is extracted from the guiding element, the needle unit is removed, against the resistance of the locking position, and can drop out of the blocking device along the exit part of the groove.

In another preferred embodiment of the removing device in accordance with the invention, a cylindrical guiding element comprising an insertion opening for the injection pen is arranged over the opening. The guiding element preferably comprises a receiving tube for the injection pen, arranged such that it can be shifted within the guiding element. The receiving tube has an upper end which protrudes through the insertion opening and out of the guiding element, and a lower end which lies inside the guiding element and comprises protrusions directed inwards. Once inserted into the receiving tube, the injection pen rests on said protrusions, for example via its casing, such that the needle unit protrudes past said protrusions and out of the receiving tube and is directed towards the blocking device in the opening. Lateral protrusions can be arranged on the outer circumference of the receiving tube, said protrusions abutting the inner surface of the guiding element, such that the receiving tube is guided by the guiding element. The axial movement of the receiving tube counter to the insertion direction is then limited by edges protruding radially inwards on the insertion opening of the guiding element, wherein the lateral protrusions of the receiving tube, which protrude outwards, abut said edges. In the insertion direction, the movement is limited by the lower end of the receiving tube abutting the removing device, wherein the needle unit engages with the blocking device in the opening of the removing device and then establishes a blocking connection with said blocking device.

Using the guiding element and the receiving tube, the injection pen can be positioned exactly over and inside the blocking device. This facilitates inserting the pen into the blocking device and because it is exactly guided, the blocking connection requires less force of pressure.

It is advantageous to arrange a biasing element such as for example a spiral spring between the receiving tube and the guiding element. The spiral spring can engage via one end with a lower end of the guiding element and via its other end with the lateral protrusions of the receiving tube. After the injection pen has been inserted into the receiving tube and as the receiving tube is further guided within the guiding element, the spiral spring is compressed until the needle unit engages with the blocking device. When extracting the injection pen, the pressing force merely has to be reduced, and the needle unit is removed from the pen by the spring force of the spiral spring, such that removing the needle unit from the injection pen is facilitated.

As an alternative to the spiral spring, a lever arrangement for activating the receiving tube can be provided in the wall of the guiding element for this purpose. Preferably, the lever can be arranged in a lower area through the wall of the guiding element. When the needle unit engages with the blocking device, the interior end of the lever can for example engage with a lower area of the receiving tube, wherein the external end of the lever can be activated from the outside, such that the receiving tube can again be pushed out of the guiding element. Such a lever can further facilitate removing the needle unit.

The object of the present invention is also solved by a container for storing at least one used needle unit of an injection pen, wherein the container comprises a feeding opening which is provided with a device for removing the needle unit from the injection pen such as has been described above. A needle unit can be inserted into such a container without the user coming into contact with the needle. A used needle unit from the injection pen can be dispensed into the container, to be subsequently disposed of, by a simple hand operation and can therefore be performed quickly and efficiently.

In a container in accordance with the invention, it is on the one hand possible that once the injection pen has been extracted from the removing device, the blocking connection between the needle unit and the blocking device is broken and the needle unit is released, such that it remains loose in the container. On the other hand, the needle unit can be released from the injection pen in such a way that, once the injection pen has been extracted from the guiding element, the needle unit remains in a blocking connection with the blocking device and is only pushed out of or relative to said blocking connection by an injection pen subsequently inserted into the container. A container can of course also be dimensioned such that it can only accommodate one needle unit.

The container can particularly advantageously form a system comprising a transport box which accommodates the container and comprises a repository for unused needle units. A conventional box or carton can for example be used as the transport box. The height of the transport box is preferably adjusted to the height of the container, such that the container is easily accessible when the transport box is opened. When the container is accommodated in the transport box, sufficient space remains in the transport box in which unused needle units can be stored as supplies. The volumetric capacity of the container for used needle units and the volumetric capacity of the repository for unused needle units are preferably adjusted to each other. This means that the repository should not be able to accommodate a greater number of unused needle units than the number of used needle units which can be disposed of in the container. In this way, the system consisting of the container and the transport box forms a practical supply and disposal device for needle units.

BRIEF DESCRIPTION OF THE INVENTION

Preferred example embodiments of the invention are explained below on the basis of the drawings, which show:

DETAILED DESCRIPTION OF THE DRAWINGS

Figure 1:
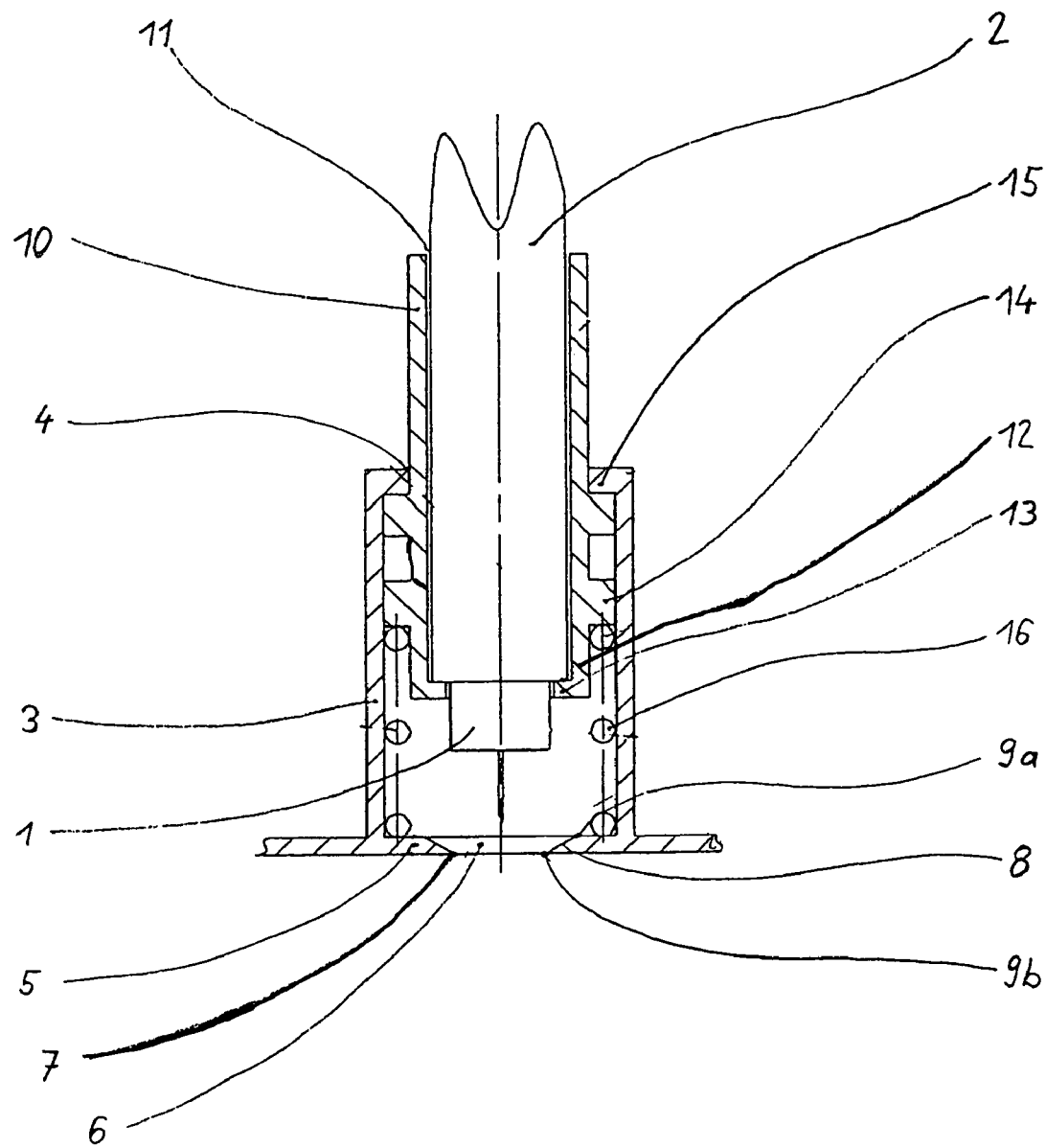
FIG. 1 shows a cross-section through a preferred embodiment of a removing device in accordance with the invention comprising a biasing element and a needle unit on the injection pen.

FIG. 1 shows a device in accordance with the invention for removing a needle unit 1 from an injection pen 2, comprising a cylindrical guiding element 3. The guiding element 3 is provided with an upper insertion opening 4 for inserting the injection pen 2 and a lower area 5 in which an opening 6 is inserted. In the opening 6, a blocking device 7 is arranged in accordance with the invention in a rim area. The blocking device 7 extends over the whole circumference of the rim 8 of the opening 6. In some embodiments, the blocking device 7 forms a locking structure substantially coextensive with the circumference of the rim 8 area of the opening.

In this example embodiment, the blocking device 7 is provided by a rim 8 of the opening 6 which is conically constricted outwards, i.e. the rim 8 of the opening 6 in the area 5 of the guiding element 3 exhibits a larger circumference on the interior edge 9a than on the exterior edge 9b.

In this preferred embodiment, a receiving tube 10 for the injection pen 2 is arranged in the guiding element 3 and can be shifted within the guiding element 3. An upper end 11 of the receiving tube 10 protrudes through the upper opening 4 of the guiding element 3 and out of the guiding element 3. A lower end 12 lies inside the guiding element 3 and comprises protrusions 13 directed inwards, on which the injection pen 2 rests when inserted into the receiving tube 10. The needle unit 1 of the inserted injection pen 2 protrudes past the protrusions 13 and out of the receiving tube 10, towards the blocking device 7.

Preferably, protrusions 14 are arranged laterally on the outer circumference of the receiving tube 10 and abut the inner surface of the guiding element 3. The outer protrusions 14 serve on the one hand to guide the receiving tube 10 in the guiding element 3. On the other hand, they act as abutments for a spiral spring 16 which is inserted between the receiving tube 10 and the guiding element 3 as a biasing element for the receiving tube 10. The opposing abutment for the spiral spring 16 is formed by the lower area 5 of the guiding element 3. The coils of the spring run on the inner surface of the guiding element 3.

In FIG. 1, the injection pen 2 is completely inserted into the receiving tube 10, such that it abuts the inner protrusions 13 and positions the needle unit 1 in the direction of the blocking device 7. The spring 16 is relaxed and the outer protrusions 14 abut the edges 15 of the guiding element 3 which protrude inwards.

Figure 2:
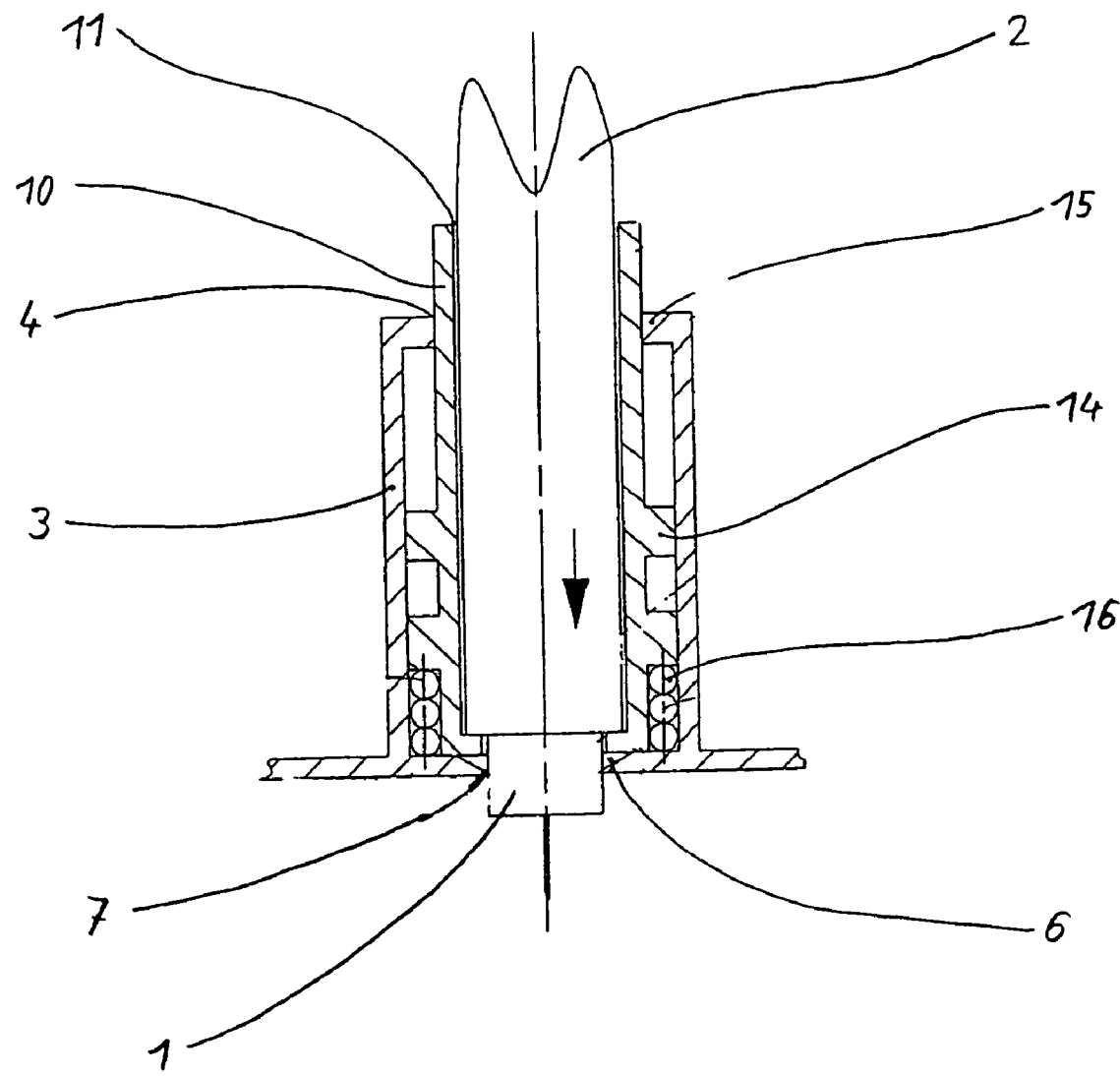
FIG. 2 shows a cross-section of the embodiment from FIG. 1, when biased.

FIG. 2 shows the removing device from FIG. 1, wherein the needle unit 1 now engages with the blocking device 7, through the opening 6. To this end, the receiving tube 10 has been shifted by a manual force counter to the spring force of the spiral spring 16 inside the guiding element 3, in the direction of the arrow shown, until the lower end 12 of the receiving tube 10 abuts the lower area 5 of the guiding element 3, and the needle unit 1 protruding downwards out of the receiving tube 10 is pressed through the opening 6 into the blocking device 7. This creates a blocking connection between the needle unit 1 and the blocking device 7. When the needle unit 1 is pressed into the blocking device 7, the spiral spring 16 is biased.

Figure 3:
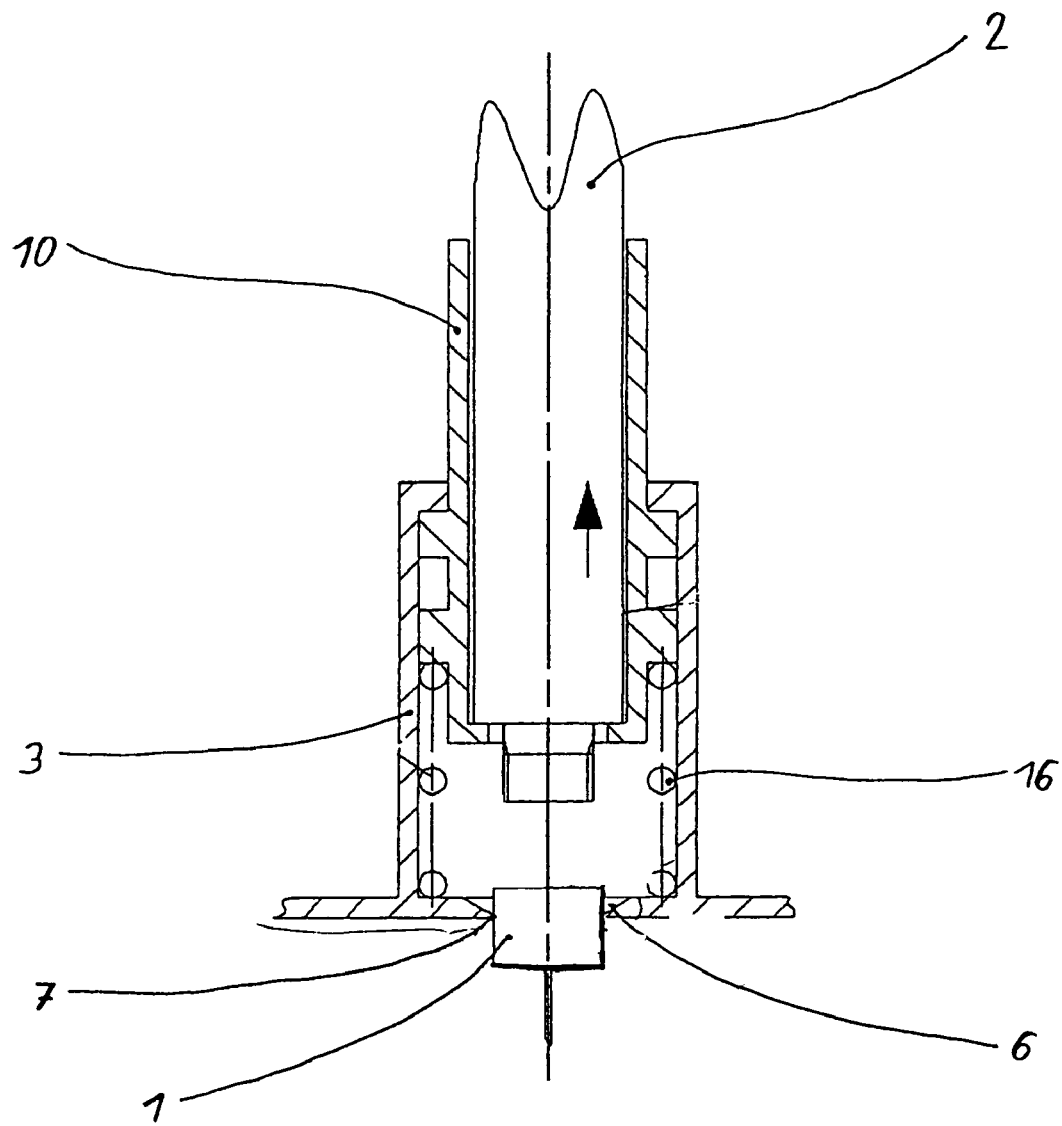
FIG. 3 shows a cross-section of the embodiment from FIG. 1, with a needle unit removed.

FIG. 3 shows the removing device with a needle unit 1 removed. In order to remove the needle unit 1 from the injection pen 2, it is merely necessary to reduce the force being manually exerted on the injection pen 2, since the receiving tube 10 is automatically pushed out of the guiding element 3 in the direction of the arrow shown by the spring force of the spiral spring 16. The blocking device 7 acts as holding claws on the needle unit 1, such that the needle unit 1 is removed from the injection pen 2 when the injection pen 2 is moved back. As is shown in FIG. 3, the needle unit 1 can remain in the blocking device 7 and is only pushed out of the blocking device 7 by the needle unit of another injection pen being inserted.

Figure 4:
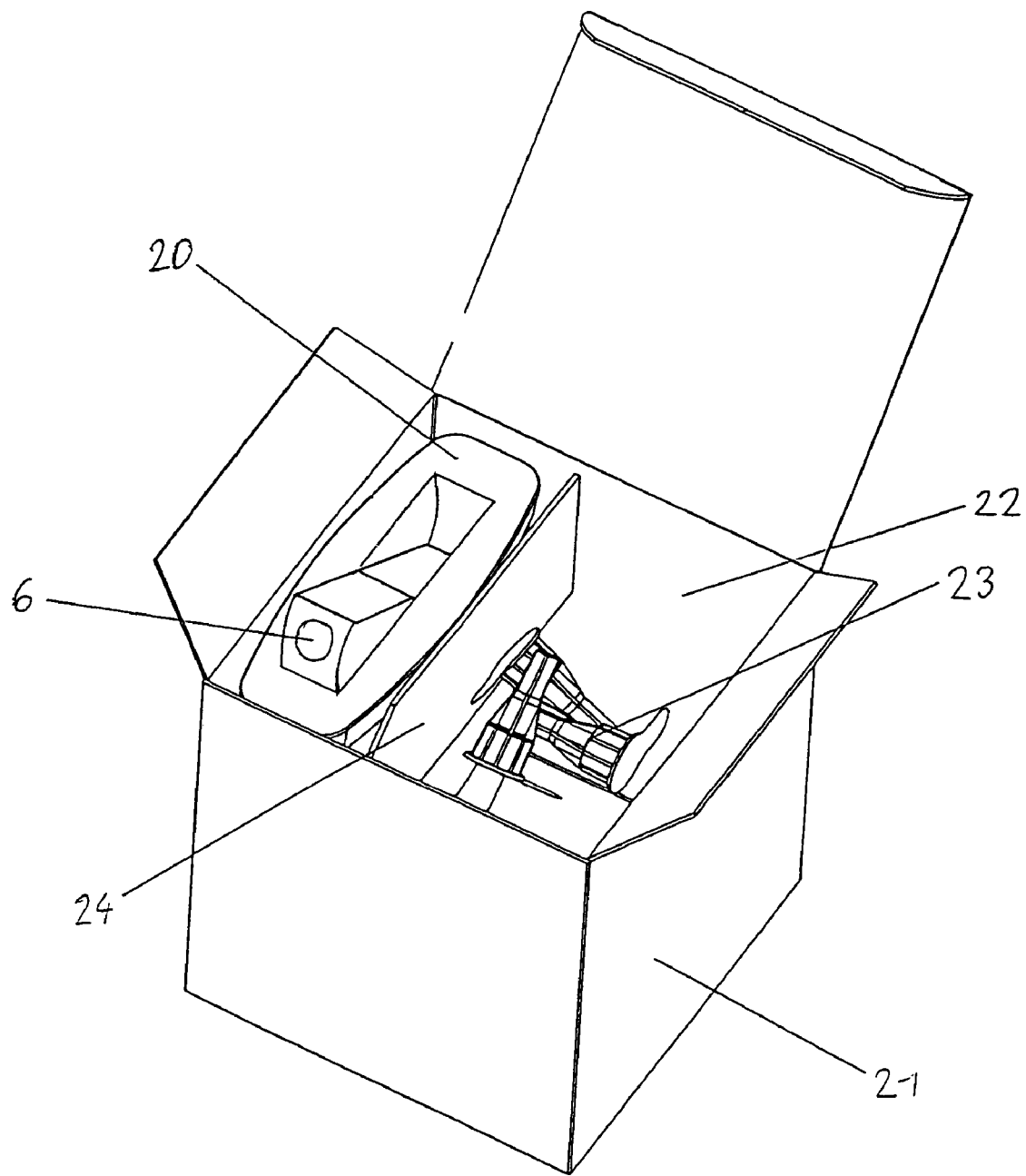
FIG. 4 shows a system consisting of a container, including and needle removing device, and a transport box.

FIG. 4 shows a system consisting of a container 20 and a transport box 21 which accommodates the container 20 and comprises a repository 22 for unused needle units 23. The height of the transport box 21 substantially corresponds to the height of the container 20. A partition wall 24 secures the container 20 on one side of the transport box 21. The remaining space on the other side of the transport box 21 forms the repository 22. In the example shown, the container 20 comprises a tilting device using which a removal device comprising an opening 6 and a blocking means in accordance with the invention can be swung out, such that the opening 6 is accessible from the outside. The container 20 therefore does not have to be removed from the transport box 21 in order to dispose of a used needle unit. Once a used needle unit from an injection pen has been disposed of with the aid of the removing device of the container 20, the tilting device can be retracted again, such that the opening 6 of the removing device is embedded in the container. The container 20 is preferably fixedly sealed and cannot be opened, in order that the used needle units are inaccessible. As many unused needle units 23 can be accommodated in the repository 22 as can be disposed of in the container 20 once used.

Figure 5:
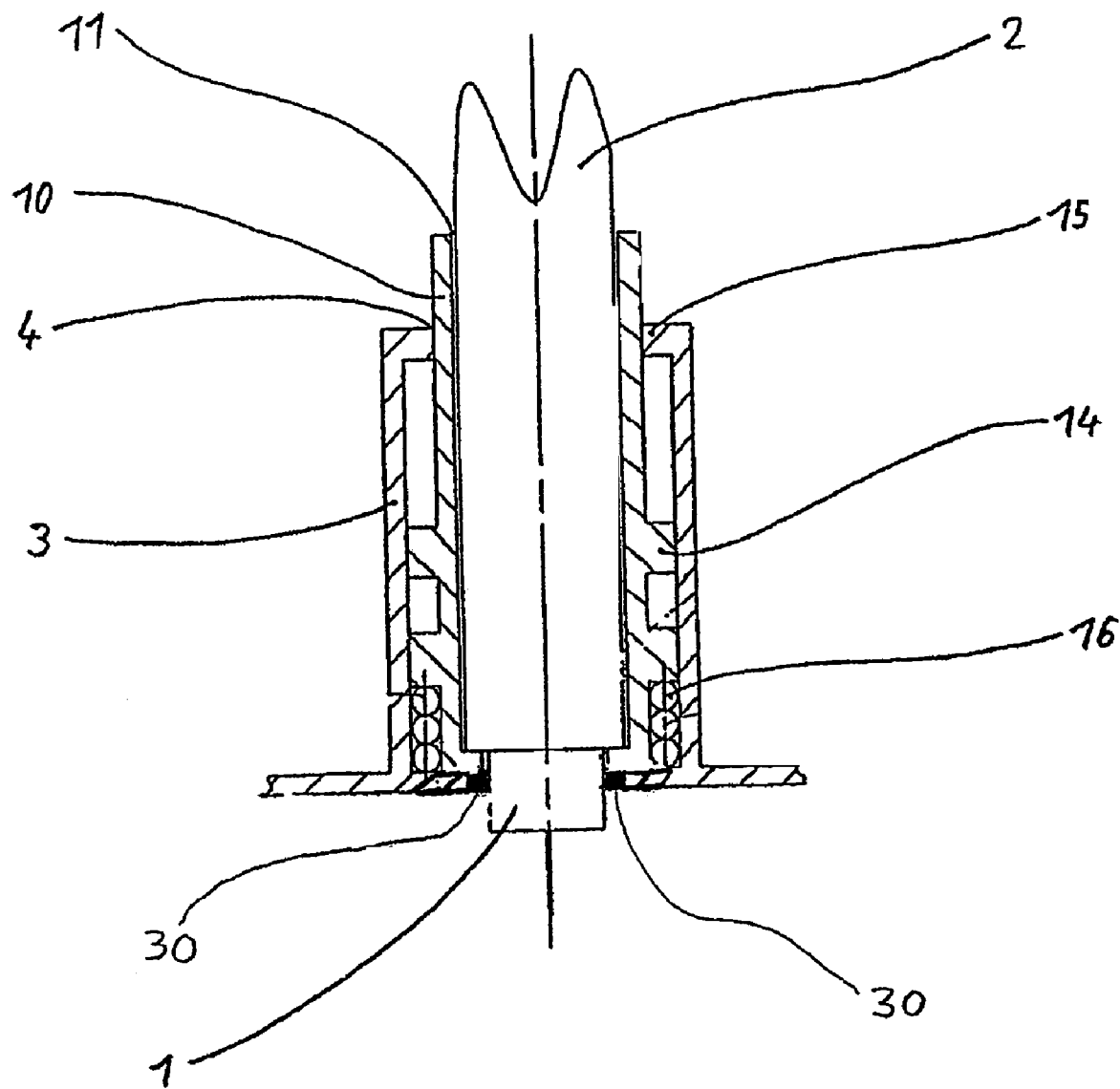
FIG. 5 shows a cross-section of an embodiment of a removing device in accordance with the invention.

FIG. 5 shows a device in accordance with an embodiment of the invention. In this embodiment, a blocking device using one or more rubber elements 30 arranged on the rim surface of the opening are provided. When the needle unit 1 is pressed into the blocking device, the rubber element 30 is compressed and establishes a clamping connection with the needle unit 1.

Figure 6:
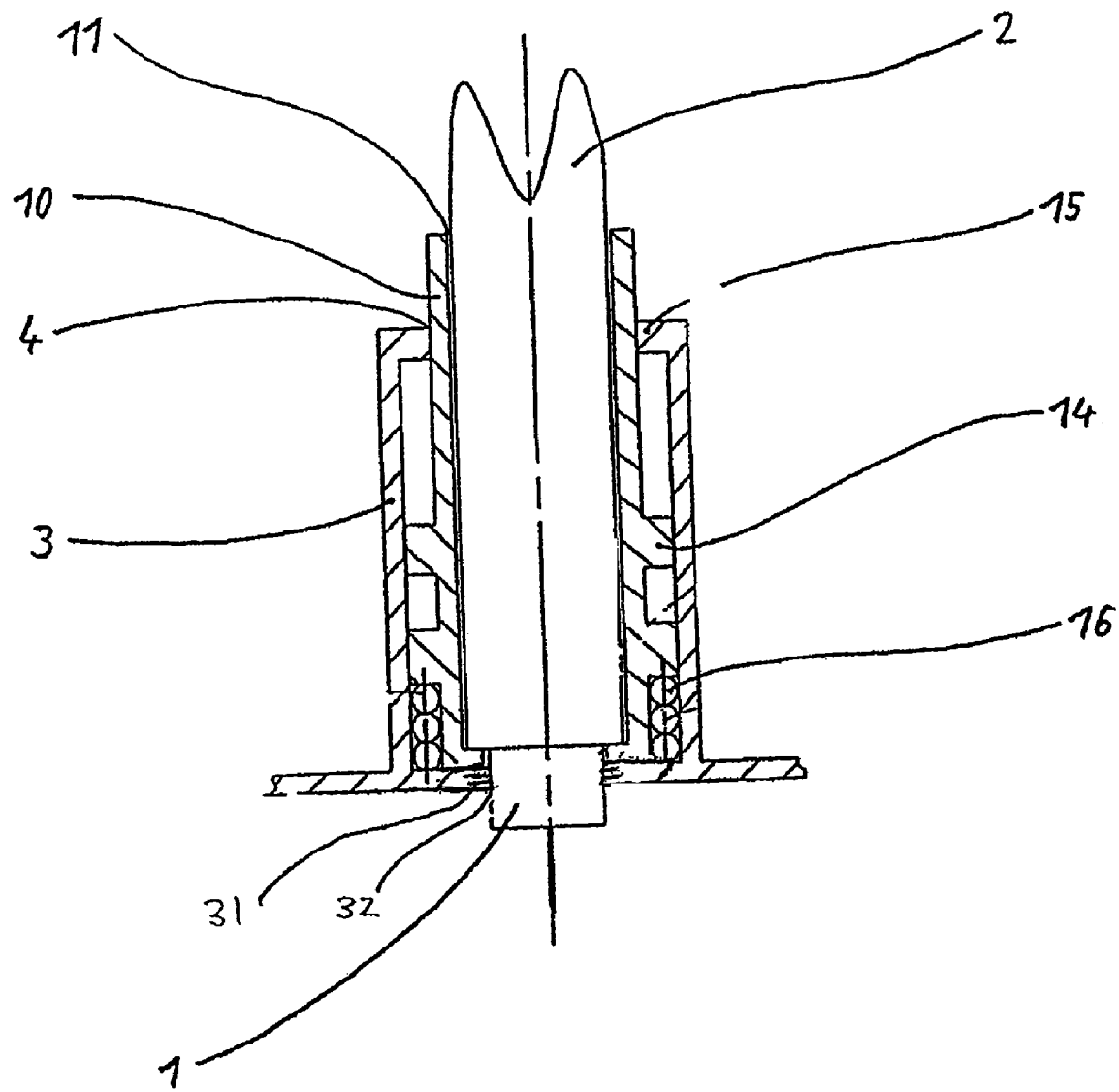
FIG. 6 shows a cross-section of an embodiment of a removing device in accordance with the invention.

FIG. 6 shows a device in accordance with an alternative embodiment of the invention wherein the blocking device is realised on the opening by a locking means which co-operates with a complementary locking means on the needle unit. For example, in FIG. 6, the locking means of the blocking device is realised by a number of grooves 31 arranged in the circumferential direction on the rim surface of the opening. The complementary locking means of the needle unit 1 are provided by a number of protrusions 32 arranged in the circumferential direction on the outer surface of the needle unit 1. In this embodiment, the blocking connection between the blocking device and the needle unit 1 may be broken by a needle unit subsequently inserted into the opening.

Figure 7:
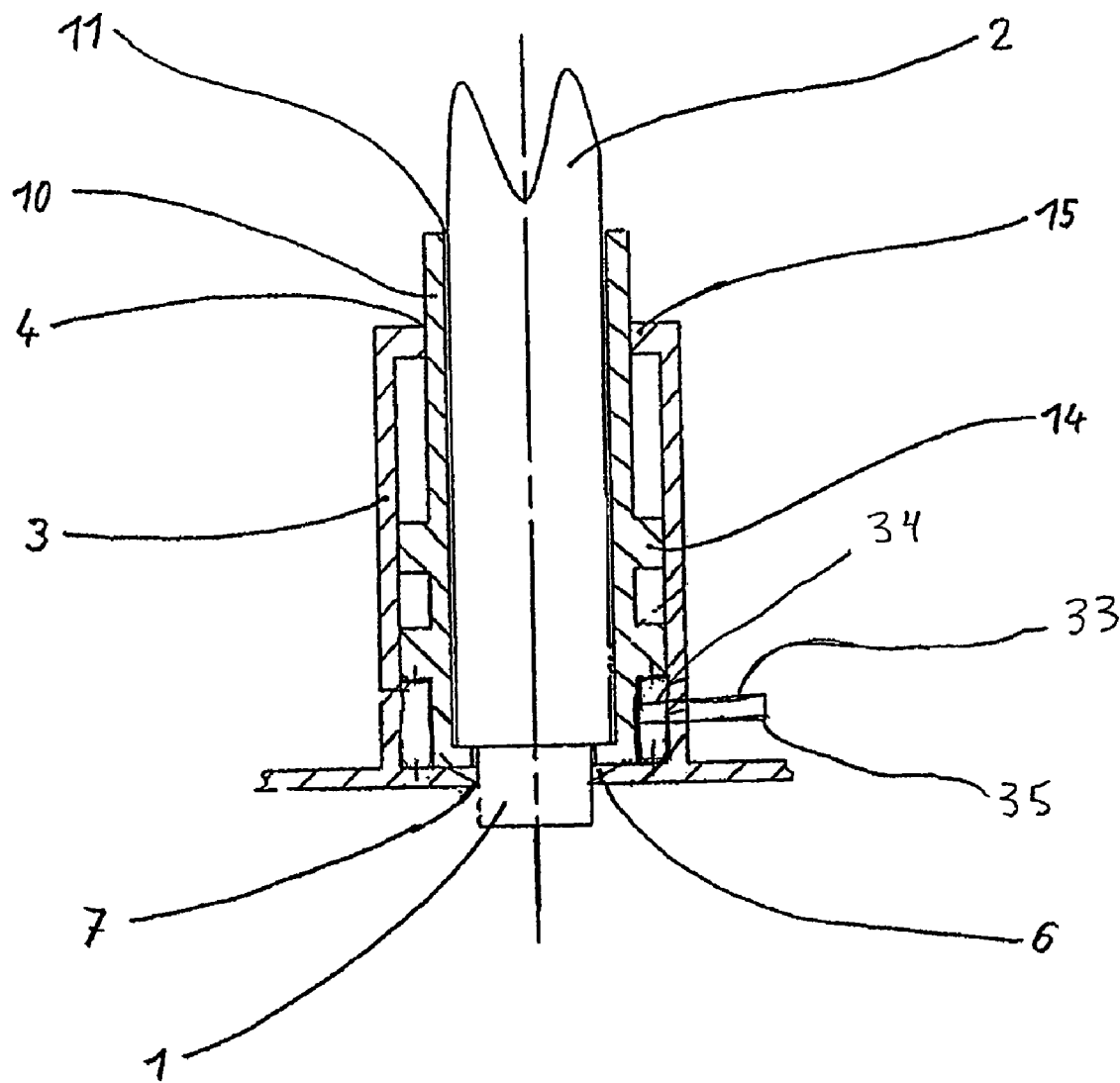
FIG. 7 shows a cross-section of an embodiment of a removing device in accordance with the invention.

FIG. 7 shows a device in accordance with a further embodiment of the invention. In the embodiment of FIG. 7, as an alternative to the spiral spring, a lever arrangement 33 for activating the receiving tube 10 is provided in the wall of the guiding element 3. In this embodiment, the lever 33 is arranged in a lower area through the wall of the guiding element 3. When the needle unit engages with the blocking device, the interior end of the lever 34 engages with a lower area of the receiving tube 10, and an external end of the lever 35 may be activated from the outside, such that the receiving tube 10 may be pushed out of the guiding element 3.

It is of course also possible for the system consisting of the container and the transport box to be formed by a unified box, and/or to provide a container with its own repository. To this end, the box and/or container is sub-divided into two areas by a partition wall. One area is fixedly sealed and comprises a removing device in accordance with the invention, preferably as a part of a tilting device, for used needle units. The unused needle units can be accommodated in the other area. This area can be sealed with the aid of a cover which, however, can be opened. The volumetric capacities of the two areas are again adjusted to each other, such that the number of unused needle units, once used, can be accommodated in the sealed area together with the removing device. If no more unused needle units are available, the area for the used needle units is full, and the box and/or container as a whole can be disposed of.

While exemplary embodiments, including preferred embodiments, of the present invention have been described herein, it is contemplated that various modifications could be made without deviating from the spirit of the present invention. Accordingly, it is intended that the scope of the present invention be dictated by the appended claims.

The invention claimed is:

1. A device for removing a needle unit from an injection device, comprising:
    an opening for receiving the needle unit and a locking structure non-shiftably arranged on the device and formed in at least one rim area along the circumference of the opening;
    a cylindrical guiding element for receiving the injection device, said guiding element generally aligned with the opening, wherein the guiding element comprises a receiving tube for receiving the injection device shiftably arranged within the guiding element, said receiving tube comprising:
        an upper end which protrudes through the guiding element; and
        a lower end which lies inside the guiding element and comprises protrusions directed inwardly, on which the injection device can rest, such that the needle unit protrudes past said protrusions and out of the receiving tube, in the direction of the locking structure; and
    a biasing element comprising a spiral spring arranged between the receiving tube and the guiding element;
    wherein the needle unit can be moved in an insertion direction after being inserted into the opening to form a blocking connection with the locking structure, and wherein the biasing element can cause movement of the injection device counter to the insertion direction, thereby breaking the blocking connection and releasing the needle unit.

2. The device as set forth in claim 1, wherein the locking structure is substantially coextensive with the circumference of the rim area of the opening.

3. The device as set forth in claim 1, wherein the locking structure comprises at least one rim area of the opening conically constricted in the insertion direction.

4. The device as set forth in claim 1, wherein the locking structure comprises locking means cooperatively engageable with complementary locking means on the needle unit.

5. The device as set forth in claim 1, wherein the locking structure comprises at least one compressible rubber element arranged on the rim area of the opening.

6. The device as set forth in claim 1, wherein the locking structure comprises a rotational connection between the opening and the needle unit.

7. The device as set forth in claim 1, wherein the locking structure of the device for removing the needle unit comprises locking means cooperatively engageable with complementary locking means on the needle unit to form the blocking connection, and wherein the locking means comprises a number of grooves arranged in a rim surface of the opening of the device and the complementary locking means comprises a number of protrusions arranged in the circumferential direction on an outer surface of the needle unit.

8. The device as set forth in claim 1, wherein the non-shiftably arranged locking structure is adjustable to an outer circumference of the needle unit.

9. A device for removing a needle unit from an injection device, comprising:
    an opening for receiving the needle unit and a locking structure non-shiftably arranged on the device and formed in at least one rim area along the circumference of the opening;
    a cylindrical guiding element for receiving the injection device, said guiding element generally aligned with the opening, wherein the guiding element comprises a receiving tube for receiving the injection device shiftably arranged within the guiding element, said receiving tube comprising:
        an upper end which protrudes through the opening and out of the guiding element; and
        a lower end which lies inside the guiding element and comprises protrusions directed inwardly, on which the injection device can rest, such that the needle unit protrudes past said protrusions and out of the receiving tube, in the direction of the locking structure; and a biasing element comprising a lever for activating the receiving tube, the lever comprising an interior end and an exterior end, wherein the lever is in a lower area of a wall of the guiding element and passes through the wall, wherein the interior end is arranged between the receiving tube and the guiding element and engages with the receiving tube when the needle unit engages with the locking structure, and wherein the exterior end can be manipulated, such that the receiving tube can be pushed relative to the guiding element;

wherein the needle unit can be moved in an insertion direction after being inserted into the opening to form a blocking connection with the locking structure, and wherein the biasing element can cause movement of the injection device counter to the insertion direction, thereby breaking the blocking connection and releasing the needle unit.

10. The device as set forth in claim 9, wherein the locking structure is substantially coextensive with the circumference of the rim area of the opening.

11. The device as set forth in claim 9, wherein the locking structure comprises at least one rim area of the opening conically constricted in the insertion direction.

12. The device as set forth in claim 9, wherein the locking structure comprises locking means cooperatively engageable with complementary locking means on the needle unit.

13. The device as set forth in claim 9, wherein the locking structure comprises at least one compressible rubber element arranged on the rim area of the opening.

14. The device as set forth in claim 9, wherein the locking structure comprises a rotational connection between the opening and the needle unit.

15. The device as set forth in claim 9, wherein the locking structure of the device for removing the needle unit comprises locking means cooperatively engageable with complementary locking means on the needle unit to form the blocking connection, and wherein the locking means comprises a number of grooves arranged in a rim surface of the opening of the device and the complementary locking means comprises a number of protrusions arranged in the circumferential direction on an outer surface of the needle unit.

16. The device as set forth in claim 9, wherein the non-shiftably arranged locking structure is adjustable to an outer circumference of the needle unit.

* * * * *